US008258123B2

(12) United States Patent
Windisch

(10) Patent No.: US 8,258,123 B2
(45) Date of Patent: Sep. 4, 2012

(54) C-19 STEROIDS FOR COSMETIC AND FURTHER USES

(75) Inventor: Martin Windisch, Bad Krozingen (DE)

(73) Assignee: ErlaCos GmbH, Erlangen (DE)

(*) Notice: Subject to any disclaimer, the term of this patent is extended or adjusted under 35 U.S.C. 154(b) by 302 days.

(21) Appl. No.: 12/734,621

(22) PCT Filed: Nov. 12, 2008

(86) PCT No.: PCT/EP2008/009540
§ 371 (c)(1),
(2), (4) Date: May 12, 2010

(87) PCT Pub. No.: WO2009/062682
PCT Pub. Date: May 22, 2009

(65) Prior Publication Data
US 2010/0256102 A1    Oct. 7, 2010

Related U.S. Application Data

(60) Provisional application No. 61/002,882, filed on Nov. 13, 2007.

(30) Foreign Application Priority Data

Nov. 13, 2007  (EP) .................................. 07022015

(51) Int. Cl.
*A61K 31/568* (2006.01)
*A61P 17/00* (2006.01)
(52) U.S. Cl. ........................................ 514/171; 514/178
(58) Field of Classification Search .................. 514/171, 514/178
See application file for complete search history.

(56) References Cited

U.S. PATENT DOCUMENTS

| 2,762,818 | A | 9/1956 | Levy et al. |
| 5,824,326 | A | 10/1998 | Crotty et al. |
| 5,904,931 | A | 5/1999 | Lipp et al. |
| 6,586,417 | B1 | 7/2003 | Abraham |
| 2003/0199487 | A1 | 10/2003 | Abraham |
| 2003/0229063 | A1 | 12/2003 | Llewellyn |
| 2006/0018937 | A1 | 1/2006 | Friedman et al. |

FOREIGN PATENT DOCUMENTS

| DE | 44 05 898 | 8/1995 |
| EP | 0 307 135 | 3/1989 |
| JP | 62-132810 | 6/1987 |
| JP | 2006-306816 | 11/2006 |
| WO | WO-92/05763 | 4/1992 |
| WO | WO-92/07586 | 5/1992 |
| WO | WO-03/026568 | 4/2003 |
| WO | WO-2005/042741 | 5/2005 |
| WO | WO-2005/062760 | 7/2005 |
| WO | WO-2006/084312 | 8/2006 |
| WO | WO-2007/131736 | 11/2007 |
| WO | WO-2007/131737 | 11/2007 |

OTHER PUBLICATIONS

Raynaud et al., "Screening for anti-hormones by receptor studies", Journal of Steroid Biochemistry 6: 615-622.1975.
Harrison et al., "Gonadotropin-releasing hormone and its receptor in normal and malignant cells", Endocrine-Related Cancer (2004) 11 725-748.
Liang et al., "Immunocytochemical Localization of Androgen Receptors in Human Skin Using Monoclonal Antibodies Against the Androgen Receptor", The Journal of Investigative Dermatology, vol. 100, No. 5, May 1993, pp. 663-666.
Meier et al., "Recombinant Human Chorionic Gonadotropin But Not Dihydrotestosterone Alone Stimulates Osteoblastic Collagen Synthesis in Older Men with Partial Age-Related Androgen Deficiency", The Journal of Clinical Endocrinology & Metabolism 89(6):3033-3041.
Flamm et al., "An Urodynamic Study of Patients with Benign Prostatic Hypertrohy Treated Conservatively with Phyto Therapy or Testosterone", Wiener Klinische Wochenschrift, 91(18), 1979, pp. 622-627 (German).
Flamm et al., "An Urodynamic Study of Patients with Benign Prostatic Hypertrohy Treated Conservatively with Phyto Therapy or Testosterone", Wiener Klinische Wochenschrift, 91(18), 1979, pp. 622-627, XP008089756, ISSN: 0043-5325 (Partial Translation).
Mitamura et al., "Determination Method for Steroid 5α-Reductase Activity Using Liquid Chromatography/Atmospheric Pressure Chemical Ionization-Mass Spectrometry", Analytical Sciences, Oct. 2005, vol. 21, pp. 1241-1244.
Itami et al., "Role of androgen in mesenchymal epithelial interactions in human hair follicle", Journal of Investigative Dermatology, Symp. Proc., 10(3), 2005, pp. 209-211 (English Abstract-PubMed).
Ando, et al., "Expression of mRNA for androgen receptor, 5α-reductase and 17β-hydroxysteroid dehydrogenase in human dermal papilla cells", British Journal of Dermatology, 141(5), 1999, pp. 840-845 (English abstract-Wiley InterScience).
Itami et al., "Mechanism of action of androgen in hair follicles", Journal of Dermatological Science, 7 Suppl., Jul. 1994, pp. 98-103, (English abstract-unboundMedline).
Viennet et al., "Contractile forces generated by striae distensae fibroblasts embedded in collagen lattices", Archives of Dermatological Research, 297(1), 2005, pp. 10-17 9English abstract-springer).

(Continued)

*Primary Examiner* — Raymond Henley, III
(74) *Attorney, Agent, or Firm* — Edwards Wildman Palmer LLP; George W. Neuner

(57) ABSTRACT

The present invention relates to novel uses of C-19 steroid compounds, in particular C-19 steroids having an androsten-17-($OR_4$)-3-one structure for cosmetic and further uses, wherein $R_4$ is hydrogen or an unsubstituted or substituted alkyl, aryl, acyl or any group leading to hydroxyl upon biological metabolization or chemical deprotection. The present invention particularly relates to selected C-19 steroids displaying properties of high binding affinity to androgen receptor to block dihydrotestosterone from binding, while at the same time providing anabolic effects, which is useful for certain applications, particularly for influencing or controlling problems of the skin and its skin-associated body structures like cellulite, wrinkles, adipose fat tissues, hair follicles or hair growth; for influencing or controlling gland function and activity such as the sebaceous gland and other glands affecting the skin and/or perspiration. The present invention also describes a composition comprising a combination of such a compound and dimethyl isosorbide.

33 Claims, No Drawings

OTHER PUBLICATIONS

Natsch et al., "A Specific Bacterial Aminoacylase Cleaves Odorant Precursors Secreted in the Human Axilla*", The Journal of Biological Chemistry, vol. 278, No. 8, Issue of Feb. 21, 2003, pp. 5718-5727.

Beier et al., "Localization of steroid hormone receptors in the apocrine sweat glands of the human axilla", Histochemistry and Cell Biology, 123(1), 2005, pp. 61-65.

Labrie et al., "Intracrinology and The Skin", Hormone Research, 54(5-6), 2000, pp. 218-229 (English abstract-Hormone Research).

Imperato-McGinley et al., "The Androgen Control of Sebum Production. Studies of Subjects With Dihydrotestosterone Deficiency and Complete Androgen Insensitivity", Journal of Clinical Endocrinology and Metabolism, vol. 76, No. 2, 1993, pp. 524-528.

Akamatsu et al., "Control of Human Sebocyte Proliferation In Vitro by Testosterone and 5-Alpha-Dihydrotestosterone Is Dependent on the Localization of the Sebaceous Glands", Journal of Investigative Dermatology, 99(4), 1992, pp. 509-511 (English).

Kurata et al., "Intranuclear androgen concentrations in facial skin", Journal of Dermatological Science, 2(2), 1991, pp. 75 (English abstract—ScienceDirect).

C-19 STEROIDS FOR COSMETIC AND FURTHER USES

The present invention relates to novel uses of C-19 steroid compounds, in particular C-19 steroids having an androsten-17-(OR$_4$)-3-one structure for cosmetic and further uses, wherein R$_4$ is hydrogen or an unsubstituted or substituted alkyl, aryl, acyl or any group leading to hydroxyl upon biological metabolization or chemical deprotection. The present invention particularly relates to selected C-19 steroids displaying special properties useful for certain applications, particularly for influencing or controlling problems of the skin and its skin-associated body structures like cellulite, wrinkles, adipose fat tissues, hair follicles or hair growth; for influencing or controlling gland function and activity such as the sebaceous gland and other glands affecting the skin and/or perspiration and apocrine sweat glands.

The skin, the subcutis and the adipose tissues as well as their associated functional bodies such as hair follicles, glands of different origin and function are complex organs influenced by many factors. This complexity transforms into a complexity of conventional approaches to influence and control not only the skin itself, but also its skin-related bodies, organs and tissues. One area of such conventional approaches may concentrate on hormone-dependent metabolic pathways. Even within the widespread possibilities of interacting with hormone-dependent biologic pathways, there are different levels and target sites, including for example interacting with enzymes involved in hormone biosynthesis, such as aromatase and 5α-reductase, with hormone receptors such as estrogen receptor, androgen receptor (AR), LH receptor or other receptors, or interacting more generally by systemic effects, such as by influencing gonadotropin secretion, without however being limited thereto.

Prior attempts in this field, however, suffer from problems of specificity and undesired or detrimental effects, which are particularly critical in case of cosmetic appearances of the skin, the hair and related tissues and organs such as sebaceous glands, apocrine glands and the like. Sometimes, extracts from natural origins are used, however with poorly understood or unspecific activities. In other cases, there is again a complex and poorly understood presence of both agonist and antagonist activities on hormone receptors and their consequence on downstream pathways. One attempt in this connection focus on non-steroidal selective androgen receptor modulators (SARMs).

Studying 5α-reductase and its tissue-specific expression nature in the context of dihydrotestosterone generation within the body has developed the SARMs to influence testosterone (T) and dihydrotestosterone (DHT) levels. Only cells expressing this enzyme can provide themselves with sufficient amounts of DHT. For example, substances such as steroidal finasterid or non-steroidal bicalutamide or flutamide have been widely used. So far no substance is known able to extinguish the androgenic effects of DHT as far as possible or even completely, and have anabolic effects at the same time. The closest approximation to this goal consists in substances able to increase the weight of the levator ani muscle in castrated rats and increase only slightly the weight of the shrunken prostate.

The object of the present invention therefore is to provide improved possibilities application to a range of valuable applications in order to better control and influence conditions of skin, of skin-associated body structures like adipose tissues, hair follicles and hair growth, associated gland functions and activities like those of the sebaceous gland, sweat gland and other glands affecting the skin and/or perspiration.

In order to solve the object, the present invention provides C-19 steroid compounds for particular applications as set forth in the appended claims. In the framework of these applications, use is made of particular properties that have been found to be associated with the specifically selected C-19 steroid compounds.

Without being bound to a certain theory, the concepts of the present invention is based on the following considerations.

The gene coding for the androgen receptor is situated on the x-chromosome. Since men possess only one x-chromosome, defects of this chromosome have dramatic consequences. An affected XY-fetus develops phenotypically into girl instead of a true boy.

The principal mammalian androgens are testosterone and its more potent metabolite dihydrotestosterone (DHT). The related androgen receptor (AR) is a large protein of at least 910 amino acids. Each molecule consists of a portion which binds the androgen, a zinc finger portion that binds to DNA in steroid sensitive areas of nuclear chromatin, and an area that controls transcription.

Testosterone diffuses from the circulation into the cytoplasm of any cell. Depending on the enzymes present in the cytoplasm and their activity some is metabolized to estradiol by aromatase, some reduced to DHT (5α-reductase), and some remains as testosterone (T). Both T and DHT can bind and activate the androgen receptor, though DHT does so with more potent and prolonged effect. As DHT (or T) binds to the receptor, a portion of the protein is cleaved. The AR-DHT combination dimerizes by combining with a second AR-DHT, both are phosphorylated, and the entire complex moves into the cell nucleus and binds to androgen response elements on the promoter region of androgen-sensitive target genes. The transcription effect is amplified or inhibited by coactivators or corepressors.

At puberty, many of the early physical changes in both sexes are androgenic (adult-type body odour, increased oiliness of skin and hair, acne, pubic hair, axillary hair, fine upper lip and sideburn hair).

As puberty progresses, later secondary sex characteristics in males are nearly entirely due to androgens (continued growth of the penis, maturation of spermatogenic tissue and fertility, beard, deeper voice, masculine jaw and musculature, body hair, heavier bones). In males, the major pubertal changes attributable to estradiol are growth acceleration, epiphyseal closure, termination of growth, and (if it occurs) gynecomastia. If a 46,XY fetus cannot respond to testosterone or DHT, only the non-androgenic aspects of male development begin to take place: formation of testes, production of testosterone and anti-müllerian hormone (AMH) by the testes, and suppression of müllerian ducts. At birth, a child with complete androgen insensitivity (CAIS) appears to be a typical girl, with no reason to suspect an incongruous karyotype and testosterone level, or lack of uterus.

Puberty tends to begin slightly later than the average for girls. As the hypothalamus and pituitary signal the testes to produce testosterone, amounts more often associated with boys begin to appear in the blood. The increased LH stimulates local conversion of DHEA from the adrenals and testosterone from the testes within many parts of the body into estradiol (aromatase enzyme) finally leading to distribution of adipose tissue over the body characteristic for women (hips and breasts). Little or no pubic hair or other androgenic hair appears, sometimes a source of worry or shame. Acne is rare.

Hormone measurements in pubertal girls and women with CAIS are characterized by total testosterone levels in the upper male rather than female range, estradiol levels mildly elevated above the female range, mildly elevated LH levels and normal FSH levels.

Adult women with CAIS tend to be taller than average, primarily because of their later timing of puberty. Breast development is said to be above average. Lack of responsiveness to androgen prevents some usual female adult hair development, including pubic, axillary, upper lip. In contrast, head hair remains fuller than average, without recession of scalp or thinning with age. Shallowness of the vagina varies and may or may not lead to mechanical difficulties during coitus. Although the testes develop fairly unexceptionally before puberty if not removed, the testes in adults with CAIS become increasingly distinctive, with unusual spermatogenic cells and no spermatogenesis.

There will also be some slight masculinisation of the skeleton, with proportionally longer legs and arms, and larger hands and feet than the average XY woman, and the size of teeth is closer to men than those of women. Due to the lack of androgen affects the girl will not suffer from acne or temporal balding and little or no pubic hair and auxiliary body hair will develop.

The overall effect is that complete or partial AIS women tend to be exceptionally beautiful with above average height (for a woman), long well proportioned legs, generous breasts, flashing smiles, exceptionally clear skin and luxuriantly thick scalp hair.

Women with AIS do so seem to be either unusually good at sports, or are perhaps more likely to take up sport than other women. Top female athletes have often been found to have AIS when sex tested, reportedly 1 in 500 women athletes of international standard suffer from AIS, which is an order of magnitude greater than current estimates of about 1 in 5000 AIS women in the general female population. There's actually considerable interest in this association, it is being suggested that Complete AIS represents a valuable model for female performance in sports.

Therefore, CATS or PAIS phenotype is a useful representation of a shortage of androgenic effects.

Androgens exert their effects by binding to the highly specific androgen receptor (AR). The receptor proteins have a well-defined domain organisation and high-resolution structures are available for the C-terminal ligand binding domain (LBD), with different agonist and antagonist ligands bound, and the zinc-finger DNA-binding domain (DBD).

Structural studies of the ligand-binding domain of several steroid receptors have revealed that the dynamic properties of the C-terminal helix 12 (H12) are the major determinant of the activation mode of these receptors. H12 exhibits high mobility and different conformations in the absence of ligand. Upon ligand binding, H12 is stabilized in a precise position to seal the ligand-binding pocket and finalize the assembly of the activation function (AF-2) domain. Antiandrogens can work by impeding repositioning of the mobile carboxyl-terminal helix 12 of the ligand binding pocket, which blocks the ligand-dependent transactivation function (AF-2) located in the AR ligand-binding domain.

The androgen receptor has been shown to contain two transactivation functions: one is represented by a structurally defined hydrophobic groove on the surface of the LBD, formed by residues from helices 3, 4, 5 and 12 (AF-2), while the other maps to the structurally flexible N-terminal domain (NTD) and is termed AF1. The main determinants for transactivation map to NTD. The NTD is potentially involved in multiple protein-protein interactions and the length of this domain has been positively correlated with the activity of AF1 for different members of the nuclear receptor superfamily.

All nuclear receptor superfamily members of eukaryotic transcriptional regulators contain a highly conserved activation function 2 (AF2) in the hormone binding carboxyl-terminal domain and, for some, an additional activation function 1 in the NH (2)-terminal region which is not conserved. The molecular basis of AF2 is hormone-dependent recruitment of LXXLL motif-containing coactivators to a hydrophobic cleft in the ligand binding domain. AF2 in the androgen receptor (AR) binds only weakly to LXXLL motif-containing coactivators and instead mediates an androgen-dependent interaction with the AR NH (2)-terminal domain required for its physiological function. Two α-helical regions mediate the androgen-dependent, NH (2)- and carboxyl-terminal interaction. FXXLF in the AR NH (2)-terminal domain mediates interaction with AF2 and is the predominant androgen-dependent interaction site. This FXXLF sequence and a second NH(2)-terminal WXXLF sequence interact with different regions of the ligand binding domain to stabilize the hormone-receptor complex and may compete with AF2 recruitment of LXXLL motif-containing coactivators. Testosterone is a weaker androgen than DHT because of less favourable T-dependent AR FXXLF and coactivators LXXLL motif interactions at AF2.

The ligand binding structures of the AR exhibit a certain flexibility of several residues buried in the ligand-binding pocket that can accommodate a variety of ligand structures. The ligand structure itself (dimension, presence, and position of unsaturated bonds that influence the geometry of the steroidal nucleus or the electronic properties of the neighbouring atoms, etc.) determines the number of interactions it can make with the binding domain. The geometry of the atoms forming electrostatic interactions at both extremities of the steroid nucleus seems mainly responsible for the higher affinity measured experimentally for DHT over testosterone. In contrast the androgenic steroid used in sport doping, tetrahydrogestrinone (THG) which possesses the highest affinity, establishes more van der Waals contacts with the receptor than the other steroids. DHT has a flatter structure than testosterone and therefore fits better in the ligand binding pocket.

5α-reductase, the enzyme system that metabolizes testosterone into dihydrotestosterone, occurs in two isoforms. The type 1 isozyme is composed of 259 amino acids, has an optimal pH of 6-9 and represents the 'cutaneous type'; it is located mainly in sebocytes but also in epidermal and follicular keratinocytes, dermal papilla cells and sweat glands as well as in fibroblasts from genital and non-genital skin. The type 2 isozyme is composed of 254 amino acids, has an optimal pH of about 5.5 and is located mainly in the epididymis, seminal vesicles, prostate and fetal genital skin as well as in the inner root sheath of the hair follicle and in fibroblasts from normal adult genital skin. The genes encoding type 1 and type 2 isozymes are found in chromosomes 5p and 2p, respectively, and each consists of 5 exons and 4 introns.

The type 1 isozyme is not detectable in the fetus, is transiently expressed in newborn skin and scalp, and permanently expressed in skin from the time of puberty. The type 2 isozyme is transiently expressed in skin and scalp of newborns. Type 2 is the predominant isozyme detectable in fetal genital skin, male accessory sex glands, and in the prostate, including benign prostatic hyperplasia and prostate adenocarcinoma tissues. Both isozymes are expressed in the liver, but only after birth. Mutations in type 2 isozyme cause male pseudohermaphroditism, and many mutations have been reported from various ethnic groups. The affected 46XY individuals have high normal to elevated plasma testosterone levels with decreased DHT levels and elevated testosterone/DHT ratios. They have ambiguous external genitalia at birth so that they are believed to be girls and are often raised as such. However, Wolffian differentiation occurs normally and they have epididymides, vas deferens and seminal vesicles. Virilization occurs at puberty frequently with a gender role change, probably. The prostate in adulthood is small and rudimentary, and facial and body hair is absent or decreased. Balding has not been reported. Spermatogenesis is normal if the testes are descended. The clinical, biochemical and molecular genetic analyses of 5α-reductase 2 deficiency highlight the significance of DHT in male sexual differentiation and male pathophysiology. Type 1 isoenzyme may play important roles in the androgen physiology of normally virilized males and may contribute to masculinization in type 2-deficient males at the time of puberty.

High levels of 5α-reductase activity have been detected in human apocrine glands, and the concentration of dihydrotestosterone has been found to be higher than that of testosterone in the nuclear fraction of the skin of patients who suffer from excessive or abnormal odour derived from apocrine sweat (osmidrosis). Also bone cells contain the type 1 isoenzyme. In vivo inhibition of the two isoenzymes can cause an elevated incidence of impotence, decreased libido, ejaculation disorders, and gynaecomastia. The bones remain unaffected.

The AR is widely distributed among reproductive and non-reproductive tissues, including the prostate and seminal vesicles, male and female external genitalia, skin, testis, ovary, cartilage, sebaceous glands, hair follicles, sweat glands, cardiac muscle, skeletal muscle and smooth muscle, gastrointestinal vesicular cells, thyroid follicular cells, adrenal cortex, liver, pineal, and numerous brain cortical and subcortical regions, including spinal motor neurons. This wide distribution of the receptor needs to be mapped with the particular type and concentration of cofactors that are present in each tissue and cell type. This will provide a more accurate picture of the potential nuclear receptor complex that can be assembled in each case after ligand activation.

Recently, a novel family of nonsteroidal molecules has been identified with selectivity and specificity for the AR. Using molecular screening approaches targeting the transcriptional activation of the human AR, combined with discriminatory cellular assays and medicinal chemistry structure-activity efforts, several series of distinct molecules have been synthesized that possess antagonist, agonist, or partial-agonist activity. These molecules are termed "selective androgen receptor modulators" (SARMs).

SARMs of various chemical structures have been discovered and characterized, and lead compounds with much improved specificity for AR, in vivo pharmacokinetic profiles, and higher degree of tissue selectivity have entered clinical development, and are expected to dramatically expand the clinical applications of androgens. With the rapid progress in SARM discovery and increasing demand for mechanism-based drug design, more and more research efforts have been devoted to the mechanisms of action of the observed tissue selectivity of SARMs. The different series of molecules contain individual members that display selective preferences for certain tissues or activities (i.e., trophic in muscle, strong or very weak gonadotropin feedback) and widely diverse ratios of activity in sex accessory tissues (prostate, seminal vesicles) vs. other peripheral (i.e., muscle) or central nervous system responses.

The use of anabolic steroidal androgens is difficult since it is associated with hepatotoxicity, potential for prostate stimulation, virilizing actions and other side effects resulting from their cross-reactivity to related steroid receptors. If an anabolic SARM used to treat frailty or osteoporosis were of steroidal nature it should neither be aromatizable nor reducible a position C5 of the sterol skeleton.

So far no SARM has been developed able to block androgenic effects caused by DHT (growth or loss of hair, exaggerated sebum production, growth of the prostate, growth of cancer cells) and in the same time exert anabolic effects like testosterone.

In the present invention, a certain group of C-19 steroid compounds have surprisingly found to display significant positive effects useful for many cosmetic and other uses which will be described in more detail below, in particular uses applied to the skin, the subcutis or the adipose tissues as well as their associated functional bodies or organ. The C-19 steroid compounds selected according to the present invention for these beneficial uses are based on the property of a high binding affinity towards the androgen receptor (AR), yet diminishing androgenic activities typically via an effect of blocking naturally (body-) derived androgens such as testosterone and especially dihydrotestosterone (DHT) from the AR, while at the same time exerting anabolic activities on the target tissue and organs and their environmental conditions.

According to the present invention, the use may correspondingly be determined by selecting the C-19 steroid compound having both a blocking effect against a binding of DHT towards AR (measurable by binding studies against DHT as a reference compound), and an anabolic effect (measurable e.g. by determining an enhancement on collagen production of reference cells susceptible for such enhancement, such as fibroblasts). The use may be further determined by an administrated amount suitable for effecting AR binding and anabolic effect, and by an appropriate application condition, such as type of user/patient, or type of target site or organ being AR positive (i.e. having measurable androgen receptors) or being able to transport the aforementioned activities in vivo to the designated final target site or organ within a user/patient.

The compounds having a high potency in respect of diminishing or completely abolishing androgenic effects on biological pathways, while enhancing anabolic activities on the target sites, tissues and organs of particular relevance for cosmetic and further applications, such as adipose cells, fibroblasts, epithelial cells, basal cells, bone cells and other cells (sebaceous glanda, dermal papilla cells and apocrine sweat glands), as well as organs or bodies situated in or below the skin have been surprisingly found to be associated with an androsten-17-ol-3-one structure exempting testosterone, wherein even more potent compounds to bring about the desired effects of the invention are further defined by a 1-en double bond and/or a 4-en double bond, and/or a substituent bonded to the 17-ol (hydroxyl) group within the common C-19 steroid structure.

In more preferred embodiments directed to select C-19 steroid compounds among the above-defined group of compounds which are even more potent for embodying the present invention, the C-19 steroid compound has, in addition to
(i) the blocking effect on AR combined with
(ii) the enhancement of anabolic activities,
the following effects or properties alone or in combination:
(iii) the compound is not aromatized by aromatase;
(iv) the compound is not reduced by 5α-reductase;
(v) the compound inhibits 5α-reductase;
(vi) in the form of its C-17 oxidized metabolite, the compound exhibits enhanced aromatase inhibition.

Each of the aforementioned properties (iii) to (vi) alone or in combination, when combined with the primary activities on AR blocking and anabolic enhancement, leads to a further replenishment or blocking of hormones or hormone-like metabolites, which would otherwise counteract the desired effects according to the invention. For example, when the selected compound is not metabolized by aromatase or 5α-reductase, or both, neither estrogens or estrogen-like metabolites nor androgenically active metabolites are generated at the target site, notably the skin and related organs, tissues and glands, thereby further diminishing androgenic effects while enhancing anabolic effects. Exaggerated virilisations can be effectively diminished. Additional inhibition of 5α-reductase further reduces androgenic activities. Moreover, when the compounds of the present invention are oxidizable by 17β-hydroxysteroid-dehydrogenase after application in vivo, they can be converted into more potent aromatase inhibitors, thereby additionally modulating activities at the target site valuable for certain applications.

According to the present invention, the use may correspondingly be determined by selecting the C-19 steroid compound having the aforementioned effects or properties (iii) to (vi) alone or in combination. These effects or properties (iii) to (vi) can be measured by correspondingly known methods. For example, 5α-reductase activity can be measured by a method described by Mitamura et al., Analytical Sciences 21, 1241-1244 (2005). The use according to the present invention may be further determined by a suitable administrated amount of the compound, and by an appropriate application condition, such as type of user/patient, or type of target site or organ enabling the aforementioned effects or properties (iii) to (vi) alone or in combination.

The steroidal nature of the compound of the present invention implicates some additional advantages. For example the quality to be converted intracellularily by 17β-hydroxysteroid dehydrogenase type 2 to a more potent steroidal aromatase-inhibitor. Furthermore, there is the potential ability to exert a negative feedback on the release of gonadotropins from the pituitary gland, especially in the case of 4-hydroxytestosterone or its salts or esters. Thus the production of sex hormones is further slowed down systemically. Since the compound by itself can display anabolic effects it can compensate for the loss of testosterone and assists to block DHT. In addition, thanks to the steroid-type structure, the compound of the present invention exhibits hydrophobic properties, which may significantly assist topical administrations.

In particular embodiments of the present invention, the compound is selected from compounds having the following formula:

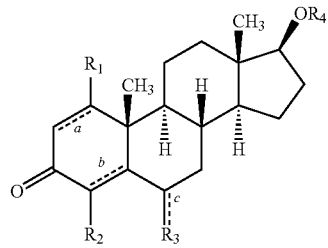

wherein
a, b and c respectively denote, independently from each other, a single bond or a double bond, with the proviso that at least one of a, b and c represents a double bond, and with the proviso that if a is single bond and b is double bond, $R_2$ is not H;
$R_1$ is hydrogen or $C_1$ to $C_6$ alkyl;
$R_2$ is hydrogen or $OR_5$, wherein $R_5$ is hydrogen or $C_1$ to $C_6$ straight chain or branched alkyl;
$R_3$ is, in case of c being a single bond, hydrogen or $C_1$ to $C_6$ alkyl, or in case of c being a double bond, $CHR_5$, wherein $R_5$ is the same as defined before;
$R_4$ is hydrogen, $C_1$ to $C_6$ alkyl, phenyl unsubstituted or substituted by $C_1$ to $C_6$ alkyl, $COR_6$ acyl group ($R_6$ being hydrogen; $C_1$ to $C_6$ straight chain or branched alkyl; phenyl or benzoyl respectively unsubstituted or substituted by $C_1$ to $C_6$ alkyl), or any group leading to hydroxyl upon biological metabolization or chemical deprotection;
and salts thereof.

In terms of a preferable consistency of being surely not aromatized, yet ensuring strong affinity to AR while having potency for satisfying conditions (iv) to (vi) mentioned above, compounds are preferably selected wherein b is a double bond, $R_2$ is hydroxyl and/or $R_3$ is methylene group, and $R_4$ is hydrogen, $C_1$-$C_6$ alkyl or $C_1$-$C_6$ acyl group. Particularly preferred are 4,17β-dihydroxyandrost-4-en-3-one (4-hydroxytestosterone; 4OHT) (wherein a is single bond, b is double bond and c is a single bond, $R_2$ is OH and $R_4$ is hydrogen) and 17β-hydroxy-6-methylenandrost-1,4-diene (wherein a and b are double bonds, $R_2$ and $R_4$ respectively are hydrogen) and the corresponding esters (such as $R_4$ denoting $COR_6$ acyl group as defined) and salts.

In case of the particularly preferred compound according to the present invention, 4OHT and its salts and esters, further use can be made, if desired, from an effect which results in a negative feedback on gonadotropin secretion.

Compounds of the present invention also include those which are metabolized to the above-defined compounds.

Moreover, it preferred that compounds are used which have predominantly anabolic activities on target cells, rather than mere androgenic effects. Further preferable are compounds which also display apoptotic effects on target cells.

Not only in theory but also in practice the compounds of the present invention and in particular 4-OHT and its related analogous compounds are the ideal anabolic substances. It remains as it is and it escapes aromatization or 5α-reduction. In binding with higher affinity to the AR than DHT without substantially exerting obut even by banning the slightest androgenic effect, it prevents the binding of DHT to this receptor, yet its binding to the androgen receptor leads substantially or even exclusively to anabolic effects. This can be deduced from three different topical applications to the skin. In the skin areas over the buttocks it anabolically increases the concentration of collagen fibres, in the apocrine sweat glands in the axilla it immediately prevents the androgen dependent production of volatile fatty acids responsible for the more or less unpleasant body odour and in the face and other acne-prone skin areas it reduces size and capability of sebaceous glands. Since the apocrine glands and the sebaceous glands exhibit type 1 activity of the corresponding isoenzyme of 5α-reductase thereby producing DHT, the observed effects could be due to an inhibition of this isoenzyme. The immediate precursor of 4-OHT and a close relative is 4-hydroxyandrostenedione, known to be able to inhibit 5α-reductase. 4-OHT is also able to inhibit this enzyme (probably both isoforms).

Although EP0307135A may partly disclose some compounds which may fall under the aforementioned formula, its therapeutic concept deal with aromatase inhibition alone or, if related to a possible androgenic activity, with an inhibitory effect on estrogen biosynthesis through a decrease in gonadotropin secretion (i.e. systemic effects, necessitating actions via generative glands, ovaries, LH-associated effects and the like). The concepts of the present invention however differ, and thus compounds are selected by distinctly different selection criteria in terms of effects exerted directly at the site of interest by considerations directed to, alone or in combination, receptor status of target cells or tissues; mode of administration; group of persons to be treated; and certain indicated uses.

A disclosure of U.S. Pat. No. 2,762,818A does not go beyond using 4-hydroxytestosterone and its esters to treat an androgen deficiency status itself as a medical implication. The special property of being neither aromatized to estrogens nor reduced to DHT is not mentioned since these metabolic pathways were unknown at this time (1956). In addition there was neither a purpose nor a finding which would suggest an androgen-blocking activity from which the uses according to the present invention could have been deduced. Further, US2003/0229063A addresses low androgen to estrogen ratios in men (leading to endocrine disorders) and only for this purpose attempts to make use of 4-hydroxytestosterone based on an asserted direct aromatase-inhibiting effect alone in the purpose to reduce estrogen levels.

In WO 2005/062760 incorporated herein in its entirety by way of reference, possible roles of androgen receptor (AR) in prostate carcinogenesis and breast cancer is discussed, and methods for breast cancer diagnosis by assaying the presence of AR are presented. However, in terms of therapeutic concepts, WO 2005/062760 is limited to control AR itself, not androgen mediated activity, in the context of mammary gland development by inhibiting AR activity. Moreover, US 2003/0199487A1 seeks to gradually increase androgen levels for the promotion of fat free mass and athletic performance without side effects associated with DHT, via 4-hydroxyandrostenedione metabolite and 4-androstenedione precursor hormone.

The compounds used according to the present invention preferably have a binding affinity to the androgen receptor (AR) higher than DHT; more preferably the binding affinity is high by having affinity specific to AR in a range of $IC_{50} \geqq 500$ nM, preferably $IC_{50} \geqq 100$ nM and more preferably $IC_{50} \geqq 50$ nM, wherein $IC_{50}$ is defined as the concentration of the compound required to reduce specific binding of a reference compound, 5α-dihydrotestosterone (DHT), by 50%. The $IC_{50}$-values can be determined by known methods using radioactively labelled DHT as reference compound, for example by a standard dextran-coated charcoal adsorption method as described by Raynaud et al., J. Steroid Biochem. 6, 615-622 (1975), using 1 nM reference concentrations of radiolabeled [$^3$H]-DHT, or by similar $IC_{50}$ determination methods described in the literature. Because the concentration of AR in the target cell is very low, typically in the nanomolar range approximately, differences in binding constants to the order contemplated in the present invention are significant.

If not known from other information or data, receptor status of target cells or target tissues with respect to AR and possibly other receptors can be determined and, if desired, quantified by standard methods known to the person skilled in the art, including immunoassays involving AR-specific or other receptor-specific antibodies, DNA and/or RNA hybridization assays or PCR amplification tests involving AR-specific or other receptor-specific nucleic acid probes.

The compounds according to the invention shall be used in amounts effective against the indicated conditions. "Use" according to the present invention may include method of treatment or prophylaxis by the specified compounds, or of a composition containing the same as an active principle together with a suitable carrier and/or diluent, for the described uses, and it includes use in the preparation of said compositions.

In experiments carried out with the compounds of the present invention it could be shown that they had excellent skin penetration capabilities so that the desired effect could be achieved by simple topic administration of e.g. an ointment, lotion or cream etc. comprising an effective amount of a compound according to the present invention to an area of a patient in need of treatment. After topical administration, the compound(s) penetrate through the skin and concentrate in the fatty tissue. In preferred embodiments, the compound of the present invention is combined with a skin penetration enhancer.

A particularly preferred compound of the present invention, 4-hydroxytestosterone, is disclosed in e.g. U.S. Pat. No. 2,762,818 A and commercially available (e.g. from Bulk Nutrition, Graham, N.C., USA—see bulknutrition.com for further information; WINKOS GmbH D-79189 Bad Krozingen, Del.). The derivatives, in particular salts and esters of the preferred 4,17β-dihydroxyandrost-4-ene-3-one include suitable ester groups, such as straight chain, branched chain or cyclic or aromatic acyl groups like formyl, acetyl, propionyl, butyryl, pentanoyl, hexanoyl, heptanoyl and benzoyl, but are not limited thereto. The esters can be formed with the 4 and/or 17 hydroxy group, preferably with the 17 hydroxy group. Its salts and esters can also be prepared by known methods (see e.g. U.S. Pat. No. 2,762,818 A).

The compounds and preparations or compositions of the invention can be administered in a variety of forms, e.g. topically, in the form of an ointment, a cream, a lotion, a gel, a spray, a powder, an oil or a transdermal plaster, also comprising depot usage forms (including pellets); orally, in the form of tablets, capsules, sugar or film coated tablets, liquid solutions or suspensions: rectally, in the form of suppositories; parenterally, e.g. intramuscularly, or by intravenous injection or infusion. According to a preferred embodiment, the compounds of the invention are designed for topical administration.

The applied amount depends on the age, weight, conditions of the user and administration form; for example the dosage adopted for oral administration to adult humans may range from about 10 to about 150-1000 mg per application, from 1 to 5 times daily.

The invention includes preparations or compositions comprising a compound of the invention in association with a carrier or diluent.

For topical use, the composition may be formulated by including, for example, vegetable oils and fats such as almond oil, peanut oil, olive oil, peach kernel oil, castor oil; plant extracts; ethereal oils; furthermore vegetable waxes and synthetic and animal oils; fats and waxes such as stearic acid and stearate esters, lauric acid and lauric esters, sorbitane esters, ceterayl alcohols; lecithin, lanolin alcohols, carotene, fragrances, mono- or polyhydric alcohols, urea, surfactants such as Proloxamers, Tweens, and the like; preservatives and colorants etc. Formulation as an oil-in-water or water-in-oil emulsion is preferred.

Solid oral forms may for example contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatine, methylcellulose, carboxymethylcellulose or polyvinyl pyrrolidone; disaggregating agents, e.g. a starch, alginic acid, alginates or sodium starch glycolate; effervescing mixtures; dyestuffs, sweeteners; wetting agents, such as lecithin, polysorbates, laurylsulphates; and, in general, non-toxic and pharmacologically inactive substances used in pharmaceutical formulations. These preparations may be manufactured in known manner, for example, by means of mixing, granulating, tabletting, sugar-coating, or film-coating processes. The liquid dispersions for oral use may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The active compound content of a suitable composition can be between 0.0001 and 20% by weight, preferably 0.6% until 10% by weight, further preferably 1 and 5% by weight, of the compound according to the invention. A customary range is 0.6 to 5% by weight.

If substances are admixed to promote skin penetration, their content, when using hyaluronidases, can be, for example, between 0.01 and 1% by weight, preferably 0.05 and 0.2% by weight, when using dimethylisosorbide or DMSO between 1 and 25% by weight, preferably 5 and 10% by weight.

In a particular embodiment of the present invention, the compounds described above are formulated in a suitable topical administration form together with a suitable solvent. As a particularly effective solvent in terms of excellent solubility for the type of compounds according to the present invention, combined with effectively assisting epithelial penetration thereof, has been found by dimethylisosorbide (also called Arlasolve DMI; available by ICI), alone or in combination with other carriers or solvents, for example alcohols or polyols such as ethanol, polyethylene glycol, propylene glycol and mixtures thereof, and possibly other ingredients described above.

If desired, the effects described above can be supplemented by additionally using a 5α-reductase inhibitor in an effective amount sufficient to inhibit 5α-reductase, and/or an anti-androgen or SARM in an amount effective to block AR. In this respect, 5α-reductase inhibitors such as finasterid, 6-aza-steroids and other compounds known to inhibit 5α-reductase of type 1 or type 2, or to dually inhibit both type 1 and type 2 can be used in combination with the compounds described above. Further, an anti-androgen or SARM known as such can be used in combination, such as bicalutamide or flutamide In the following, preferred but non-limiting embodiments are presented, where the compounds according to the present invention can display their effects in particularly effective fields of application.

Hair Growth

Androgenic alopecia is the most frequent cause of hair loss affecting up to 50% of men and 40% of women by the age of 50. This continuous process results in a form of alopecia that follows a definite pattern in those individuals who are genetically disposed. Although clinically different, the pathogenetic pathways leading to this type of hair loss are thought to be similar in both sexes. Androgenetic alopecia can be defined as an DHT-dependent process with continuous miniaturization of sensitive hair follicles. Today there is no explanation for the fact, that DHT leads to androgenic alopecia on one side and to androgen dependent beard growth on the other side.

Androgen site-specifically affects human hair growth after puberty through androgen receptors in the dermal papilla, which transactivate target genes acting in conjunction with co-activators (Itami and Inui, J. Investig. Dermatol. Symp. Brok. 2005, 10(3), pp. 209-211). Human hair follicles, which are distributed in various and specific sites of the body, appear a marked susceptibility for androgen-dependent growth. Beard, axillary, and frontal scalp dermal papilla cells possess the characteristics of androgen target cells. These cells show strong expression of androgen receptors. The expression of 5α-reductase isotype 2 is restricted to beard and frontal scalp DPC. DPC mediate the signals of androgen to follicular epithelial cells apparently in a paracrine fashion. In beard its activity is three times higher than in occipital scalp (Ando et al., Br J Dermatol. 141(5):840-845 (1999)). The predominant enzyme in non occipital scalp and beard is the type 2 isoenzyme. Hair follicles of occipital scalp do not contain androgen receptors (Itami et al., J Dermatol Sci. 7 Suppl., S98-103 (1994)).

Without affecting the biological pathway according to the present invention, testosterone would be transferred into dihydrotestosterone via 5α-reductase locally, where the strong androgenic effect of DHT is generated. Treatment and prevention of benign prostatic hyperplasia (BPH) using finasteride, an inhibitor of the isozyme 2 of the 5α-reductase, has demonstrated that it is his enzyme which provides the hair follicles of the regions of the scalp, where androgenic alopecia occurs, with DHT. Binding of DHT to the androgen receptor in the cells of the dermal papilla of the specific areas leads to a regression of terminal hair into vellous hair (androgenic alopecia). As a consequence, the hair follicles of the scalp, though being numerically unchanged, only produce vellous hair. There is a progressive hair loss. Instead of exhausting the source of DHT, blocking of the androgen receptor against DHT is directed to a hair sparing effect or even regrowth of scalp hair. Balding hair follicle dermal papilla cells contain higher levels of androgen receptors than those from non-balding scalp. Thus, the compounds of the present invention are very valuable for promoting hair growth on the scalp.

The situation in the body regions other than the scalp however is different. Sometimes hair growing excessively on other parts of the body is a nuisance. They are conventionally removed by depilation or epilation. Hot wax epilation restores the growth of hair in many dorming hair follicles (telogen hair) thereby increasing the frequency and painfulness of hot wax epilation. Pubic and axillary hair is sparse or absent in CAIS. Corresponding cell cultures contain as androgen predominantly testosterone and only traces of DHT. Growth of unwanted hair in the corresponding body regions cannot be prevented by blocking of 5α-reductase. According to the present invention, this is possible by blocking the androgen receptor against DHT. In almost all hair follicles (with the exception of scalp, pubic and axillary hair) specific cells of the dermal papilla are driven by DHT to promote hair growth. If the corresponding areas of the skin are topically treated with for instance 4-OHT or an analogous compound of the present invention, hair sprouting from the corresponding hair follicles grow scanty, and they exhibit different structures and colours than before treatment. Body hairs grow slower and less dense and in addition thinner and blonder. After six months most of the follicles are producing solely vellous hair.

Hence, the use of the compounds according to the present invention leads to desirable effects depending on the application target, that is a reduction of the formation of terminal hairs in the region of body hairs (regions other than the scalp), whereas there is a recovery of terminal hairs on the scalp. Thus, the compounds of the present invention allow for an efficient dual effectivity on hair growth.

Cellulite and Collagen Synthesis

Cellulite is a cosmetic problem resulting from unstable subcutaneous structure and especially the region at or between adipose tissue and cutis tissue. In order to stabilize these structures, structural proteins and elastic fibers are relevant factors, and usually fibroblast cells are involved in generating such structural proteins and fibers.

It has been found that due to the presence of androgen receptors, at least partially, at relevant target cells involved in the formation of cellulite and other affected subcutaneous tissue, one can make effective use of the dual activity associated with the compounds of the present invention, namely binding to AR without however having a substantial androgenic effect, while on the other hand displaying anabolic activities on relevant target cells such as fibroblasts. Selecting the preferred steroids according to the present invention thus blocks AR against the effects of naturally derived androgens such as DHT, while preferably stimulating the generation of structural proteins and elastic fibers and in particular collagen synthesis via their anabolic effect.

Androgen receptors have been found to be present in human skin (see e.g. Liang et al., J. Invest. Dermatol. 1993, 100(5), pp. 663-666 (1993)). Furthermore, the better androgenic effects can be blocked, the more pronounced is a stimulation of anabolic effects and notably collagen formation (based on an observation made e.g. by Meier et al. in J. Clin. Endocrinol. Metab. 89(6), pp. 2033-241 (2004).

The observation that the topical treatment of the skin over the predilection areas of cellulite with a preparation containing 4-OHT leads within four weeks to a considerable solidification of the skin confirms that this preparation has an anabolic effect. The mechanism underlying this strengthening of the skin apparently is a drastic augmentation of collagen fibres in the skin accompanied by a marked diminution and shrinkage of the adipocytes entrapped in the mesh of collagen fibres. Cellulite exhibits a diffuse pattern of extrusion of underlying adipose tissue into dermis. The border between the two layers is made up of collagen fibres. Strengthening this border by increasing its collagen content by stimulating the fibroblasts to produce more collagen leads to a marked improvement of the appearance of cellulite.

A topical formulation containing a compound according to the present invention such as 4-OHT or an analogous compound can increase the collagen content of the skin via stimulation of the fibroblasts. A topical formulation containing 4-OHT has proven to be superior than 4-OHA. It is reasonable to assume that 4-OHT has solely anabolic effects. After application to the skin no androgenic effect whatsoever could be observed in this highly androgen-sensitive organ. Apparently is 4-OHT unable to exert any androgenic effects such as hair growth or pimples.

Beneficial effects can likewise be assumed for application cases where strengthening, stabilisation and/or augmentation of collagen is at issue too, i.e. also applications to the skin for purposes other than cellulite.

Strias of the Skin as Well as Atony of the Upper Skin

Striae distensae are characterized by linear, smooth bands of atrophic-appearing skin that are reddish at first and finally white. They are due to stretching of the skin, as in rapid weight gain, or mechanical stress, as in weight lifting. The pathogenesis of striae distensae is unknown. Biopsy specimens of women with striae also show a diminution of collagen (Viennet et al., Arch Dermatol Res. 297(1), 10-17 (2005)). The primary goal therefore in the treatment of striae is the stimulation of fibroblasts to produce more collagen. Conventionally, this has been tried by a 585 nm collagen remodelling, double flashlamp excited pumped dye laser. The wavelength of 585 nm corresponds to an absorption peak of haemoglobin. The heating effect in these skin layers triggers the release of various growth factors that stimulate collagen remodelling and tightening.

Striae have also been treated according to the invention with a suitable formulation containing 4-OHT. The beneficial effects on collagen synthesis lead to an increasing thickness of the skin. Whereas striae rubrae are more disturbing on a fair skin striae albae are a considerable problem for dark skin. In both cases 4-OHT and apparently analogous substances according to the present invention makes them disappear.

Skin Aging and Wrinkles

Although the prevention of skin aging is a holy grail of the cosmetic and pharmaceutical industries, this venture may be misplaced. The predominant clinical and biochemical features of aged skin are mostly attributable to photoaging rather than chronology.

Photodamaged skin had been treated for many years using treatment options such as topical treatments with preparations such as retinoids, α-hydroxy acids and antioxidants. As a second-level option, facial rejuvenation procedures such as botulinum toxin injection, soft tissue augmentation with collagen or hyaluronic acid gel, skin resurfacing, use of chemical peels, dermabrasion and laser resurfacing procedures can be used removing the epidermis and a variable thickness of dermis with dermabrasion or chemical peels, with the expectation that reepithialization and collagen remodeling will result in a more youthful appearance. Collagen was one of the first fillers for aesthetic enhancement and has been in use for more than 20 years. In recent years there has been a surge of new injectable fillers, with more anticipated in the near future. Despite the large number of new products for augmentation and wrinkle filling, there still remains a role for injectable collagen alone and in combination with other wrinkle fillers.

Instead of injecting collagen in the skin to smoothen wrinkles, a more conservative way of increasing the collagen content of the skin, where wrinkles are disturbing, it is easier to stimulate the local resident fibroblasts to produce more collagen. This can easily be achieved using topical application of a compound according to the present invention, in particular to skin regions of the face and in the décolleté.

Diminution of Adipose Tissue

4-OHT and analogous compounds according to the present invention achieve shrinkage of adipose tissue certainly not by androgenic affects. As they have pronounced anabolic effects, it is likely that such effects are responsible for the reduction of adipose tissue.

Body Odor and Use as Deodorant

Bromhidrosis, also known as bromidrosis or body odour is a common phenomenon in postpubertal individuals. In rare cases, bromhidrosis may become pathologic if it is particularly overpowering or if it significantly interferes with the lives of the affected individuals. Bromhidrosis is a chronic condition in which excessive odour, usually an unpleasant one, emanates from the skin. This condition, determined largely by apocrine gland secretion, can substantially impair a person's quality of life.

Human secretory glands are primarily divided into 2 types: apocrine and eccrine. Eccrine glands are distributed over the entire skin surface, where they are involved in thermoregulation by means of sweat production. In contrast, apocrine glands have a limited distribution involving the axilla, genital skin, and breasts. Apocrine elements are also found in the periorbital and periauricular areas. Apocrine glands have no thermoregulatory role but are responsible for characteristic pheromonal odors. Apocrine bromhidrosis is the most prevalent form and should be differentiated from the less common eccrine bromhidrosis. Several factors contribute to the pathogenesis of apocrine bromhidrosis. Bacterial decomposition of apocrine secretion yields ammonia and short-chain fatty acids, with their characteristic strong odors. The most abundant of these acids is (E)-3-methyl-2-hexanoic acid (E-3M2H), which is brought to the skin surface bound by 2 apocrine secretion odor-binding proteins (ASOB1 and ASOB2). One of these binding proteins, ASOB2, has been identified as apolipoprotein D (apoD), a known member of the lipocalin family of carrier proteins.

Axillary bacterial florae have been shown to produce the distinctive axillary odor by transforming nonodiferous precursors in sweat to more odiferous volatile acids (Natsch, 2002). The most common of these are E-3M2H and (RS)-3-hydroxy-3-methylhexanoic acid (HMHA), which are released through the action of a specific zinc-dependent N-alpha-acyl-glutamine aminoacylase (N-AGA) from *Corynebacterium* species. This aminoacylase has recently been demonstrated to also release other odiferous acids from glutamine conjugates in sweat, which may be the basis of individual body odor.

Apocrine sweat gland exhibits a high activity of 5α-reductase isotype 1. The apocrine glands of persons suffering from osmidrosis exhibit higher concentrations of DHT than of testosterone. Apocrine sweat glands exhibit the androgen receptor (Beier et al., Histochem Cell Biol. 123(1):61-65 (2005)). The endowment with androgen receptors correlates with the tallness of the epithelium. In apocrine gland a tall epithelium is connected with secretory activities.

Since especially apocrine perspiratory glands possess androgen receptors, it has been found that compounds according to the present invention enable a very fast and effective regulation of the composition of sebaceous substances affecting body odor, via their highly potent binding to AR and possibly further assisted by the co-activities associated with the compounds of the present invention.

Thus, the compounds of the present invention lend themselves as deodorants for affected body or skin regions like hair regions (especially at the axially), eccrine and especially apocrine perspiratory glands, sebaceous glands, sweat glands, etc., eventually leading to a well-balanced and neutral body odor.

The remarkably high affinity of the compound according to the present invention to the androgen receptor and the immediate effect on body odour make a 5α-reductase-inhibition, at least such an inhibition alone, less likely and speak for blocking of the androgen receptor as a primary mechanism of action.

The majority of glands relevant for body odor are situated in the subcutaneous tissue. It is therefore difficult to apply effective substances directly. To this end a substance is preferably included facilitating the penetration into the skin. Optimal results have been observed with a combination of 4-hydroxytestosterone and the substance dimethyl isosorbide (Arlasolve DMI), wherein 4-hydroxytestosterone could be likewise replaced by its salts and esters described above.

Sebaceous Glands and Skin Purity

Common acne is a steatorrhoic chronic disease, to which specific is, among others, the presence of blackheads, papulopustular eruptions, purulent cysts and cicatrices. Many medications are available for the management of acne. The armamentarium includes topical retinoids, antimicrobial and antibacterial agents, hormonal agents (oral contraceptives and spironolactone) and systemic retinoids. Acne is usually is treated with combination therapy to address its multifactorial pathophysiology. A key factor in the pathogenesis of acne is sebum production. Only isotretinoin and hormonal therapy improve acne via their actions on the sebaceous glands. In the etiopathogenesis of common/simple acne, a decisive role is played by DHT.

The human skin, especially the sebaceous gland is a stereogenic organ similar to the gonads and adrenal cortex, possessing all the enzymes required for steroid sex-hormone synthesis and metabolism (Labrie et al., Horm Res. 54(5-6), 218-229 (2000)). In complete androgen resistance the skin is especially clear. Persons with complete androgen insensitivity fail to produce sebum for instance in the skin of the forehead (Imperato-McGinley et al., J Clin Endocrinol Metab. 76(2), 524-528 (1993)).

The presence of type 1 isozyme of 5α-reductase indicates a considerable involvement of DHT in sebum production. The activity of this 5α-reductase in sebaceous glands is higher than in the surrounding skin (face, scalp, not acne-prone skin). The sebaceous glands of facial skin and the skin of the head exhibit higher enzyme activities than sebaceous gland from not acne-prone skin. In complete androgen resistance the skin is especially clear. DHT stimulates the proliferation of facial sebocytes stronger than testosterone. The proliferation of nonfacial sebocytes is inhibited by testosterone, whereas DHT enhances their growth (Akamatsu et al., J Invest Dermatol. 99(4):509-511, (1992)). Skin not subjected to the influences of androgens exhibits very low concentrations of testosterone or DHT, whereas the large sebaceous glands of the skin of the face revealed concentration comparable to genital skin. These glands are a typical androgen target organ irrespective of sex (Kurata et al., J Dermatol Sci. 2(2), 75-78 (1991)).

Topical treatment of acne has been performed with cyproterone acetate (CPA) in a 1% solution in ethanol or isopropyl myristate. It should reduce side effects currently excluding the use in males and demanding contraceptive measures in females. Cyproterone acetate so far is not able to reduce the sebum excretion rate when applied to the forehead skin of patients with acne. This can achieved by giving the drug systemically. This is an indication, that the drug is barely able to penetrate the skin. Therefore attempts are being made to load it to solid lipid nanoparticles in order to improve skin penetration (this leads to a 2-3 fold increase in CPA absorption by the skin.

The effects displayed by the compounds of the present invention, especially its blocking effect on the natural androgenic substance DHT will thus in turn counter-act a too strong production of sebaceous substances and thereby alleviating their accumulation at critical sites in or at the skin, eventually avoiding acne.

The present invention is further illustrated by the description of the following examples, which are however only for illustrative purposes and shall not be understood in any limiting manner.

EXAMPLE 1

The compound of the present invention can be synthesized as follows.

In a first step, 2.5 g testosterone is dissolved in 100 ml cold MeOH. After adding 9 ml NaOH (2%) and 17 ml $H_2O_2$ (30%) the mixture is stirred for 24 h at 4° C. The resulting epoxids are precipitated with ice-water. In a second step, 2 g of the dry epoxids are dissolved in 200 ml acetic acid containing 2% $H_2SO_4$. The solution is stirred for 4 h at room temperature. The reaction products are precipitated with ice-water. Thereafter, the reaction products are washed with 1% NaOH solution to hydrolyse the acetyl esters. The total yield of pure 4-hydroxytestosterone is in the range of 40-50%.

EXAMPLE 2

A cream for topical administration according to the invention can be formulated in conventional manner using the following amounts of ingredients. The amounts are given per 100 g of cream:

| | |
|---|---|
| 4-hydroxy-17β-acetyl-androst-4-en-3-one | 4.5 g |
| cetearyl alcohol | 7.5 g |
| paraffin wax | 3.0 g |
| sodium carbomer | 2.5 g |
| isopropyl myristate | 6.0 g |
| sorbitan monostearate | 1.0 g |
| polysorbate 20 | 3.0 g |
| stearyl alcohol | 2.0 g |
| DMSO | 5.0 g |
| purified water ad | 100.0 g |

The resulting cream can be given topically on the skin above affected skin region of a human. Given once per day in this manner, cellulite, strias or wrinkles can be controlled.

EXAMPLE 3

A gel can be formulated in conventional manner using the following amounts of ingredients. The amounts are given per 100 g of gel:

| | |
|---|---|
| 4-hydroxytestosterone | 2.5 g |
| ethanol 95% in water | 70.0 g |
| carbopol 980 | 0.5 g |
| isopropyl myristate | 2.5 g |
| triethanolamine | 0.5 g |
| purified water ad | 100.0 g |

The resulting gel can be given topically on the scalp of a man suffering from baldness. Alternatively, the resulting gel can be given topically on the skin of a woman's legs after epilation in order to slow down further hair growth at these body regions.

EXAMPLE 4

A solution for use as a deodorant spray according to the invention is prepared in conventional manner using the following formulation. The amounts are given per 100 g of solution:

| | |
|---|---|
| 4-hydroxytestosterone | 2.5 g |
| ethanol 95% in water | 70.0 g |
| isopropyl myristate | 2.5 g |
| purified water ad | 100.0 g |

The spray is applied as desired to the skin affected by unpleasant odor, such as the axialla region. Alternatively, 4-hydroxy-17β-acetyloxy-androst-4-ene-3-one (17-acetyl ester of 4-hydroxy-testosterone) can be used instead of 4-hydroxytestosterone in the amount indicated.

EXAMPLE 5

A composition is prepared by mixing the following constituents per 100 g total weight:

| | |
|---|---|
| 4-hydroxytestosterone | 7.5 g |
| dimethyl isosorbide (Arlasolve DMI) | 15.0 g |
| ethanol 95% in water | 15.0 g |
| purified water ad | 100.0 g |

The composition is used as a deodorant spray for being topically applied to the axilla affected by unpleasant body odor.

EXAMPLE 6

Tablets each weighing 0.150 g and containing 25 mg of the active substance, can be manufactured as follows (composition for 10000 tablets):

| | |
|---|---|
| 4,17β-dihydroxyandrost-4-ene-3-one | 250 g |
| lactose | 800 g |
| corn starch | 415 g |
| talc powder | 30 g |
| magnesium stearate | 5 g |

The 4,17β-dihydroxyandrost-4-ene-3-one, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets. The tablets can be used orally for cosmetic use.

EXAMPLE 7

Capsules, each dosed at 0.200 g and containing 20 mg of the active substance can be prepared (composition for 500 capsules):

| | |
|---|---|
| 4,17β-dihydroxyandrost-4-ene-3-one | 10 g |
| lactose | 80 g |
| corn starch | 5 g |
| magnesium stearate | 5 g |

This formulation is encapsulated in two-piece hard gelatine capsules and dosed at 0.200 g for each capsule. The tablets can be used orally for cosmetic use.

EXAMPLE 8

An ointment for topical administration according to the invention can be formulated in conventional manner using the following amounts of ingredients. The amounts are given per 100 g of ointment:

| | |
|---|---|
| 17β-hydroxy-6-methylenandrost-1,4-diene | 2.5 g |
| propylene glycol | 25.0 g |
| isopropyl myristate | 6.0 g |
| sorbitan monostearate | 1.0 g |
| polysorbate 80 | 2.0 g |
| stearyl alcohol | 2.0 g |
| hyaluronic acid | 0.1 g |
| purified water ad | 100.0 g |

The resulting ointment can be given topically on the skin above tissue regions affected by a deficiency of collagen.

EXAMPLE 9

An ointment for topical administration according to the invention can be formulated in conventional manner using the following amounts of ingredients. The amounts are given per 100 g of ointment:

| | |
|---|---|
| 4-hydroxy-17β-propionyloxy-androst-1,4-diene-3-one | 2.5 g |
| propylene glycol | 20.0 g |
| isopropyl myristate | 7.5 g |
| dimethyl isosorbide (Arlasolve DMI) | 10.0 g |
| stearyl alcohol | 5.0 g |
| purified water ad | 100.0 g |

The ointment can be given topically on the skin above tissue regions affected by high content of adipose cells.

EXAMPLE 10

A composition for injection according to the invention can be formulated using the following amounts of ingredients:

| | |
|---|---|
| 4,17β-dihydroxyandrost-4-ene-3-one | 10.0 mg |
| benzyl alcohol | 5.0 mg |
| polysorbate | 25.0 mg |
| sodium chloride | 10.0 mg |
| purified and sterilized water ad | 1 ml |

The thus prepared composition is injected once a week to a subcutaneous site affected by insufficient collagen content.

EXAMPLE 11

A gel for a simultaneous topical and cosmetic combination composition is formulated in conventional manner using the following amounts of ingredients. The amounts are given per 100 g of gel:

| | |
|---|---|
| 4-hydroxytestosterone | 2.75 g |
| finasterid | 1.25 g |
| ethanol 80% | 10.0 g |
| carbopol 934 P | 8.0 g |
| PEG 400 | 2.5 g |
| urea | 3.0 g |
| ethyl oleate | 0.5 g |
| purified water to | 100 g |

The gel can be applied topically on the scalp of men for enhancing hair growth.

The invention claimed is:

1. A method for the treatment of skin, skin associated body structures, hair, and skin-associated glands of a patient, the method comprising:
providing a compound selected from compounds having the following formula:

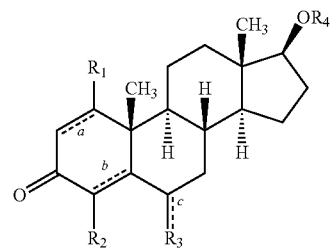

wherein
a, b and c respectively denote, independently from each other, a single bond or a double bond, with the proviso that at least one of a, b and c represents a double bond, and with the proviso that if a is single bond and b is double bond $R_2$ is not H;
$R_1$ is hydrogen or $C_1$ to $C_6$ alkyl;
$R_2$ is hydrogen or $OR_5$, wherein $R_5$ is hydrogen or $C_1$ to $C_6$ straight chain or branched alkyl;
$R_3$ is, in case of c being a single bond, hydrogen or $C_1$ to $C_6$ alkyl, or in case of c being a double bond, $CHR_5$, wherein $R_5$ is the same as defined before;
$R_4$ is hydrogen, $C_1$ to $C_6$ alkyl, phenyl unsubstituted or substituted by $C_1$ to $C_6$ alkyl, $COR_6$ acyl group ($R_6$ being hydrogen; $C_1$ to $C_6$ straight chain or branched alkyl; phenyl or benzoyl respectively unsubstituted or substituted by $C_1$ to $C_6$ alkyl), or any group leading to hydroxyl upon biological metabolization or chemical deprotection;
and salts and esters thereof; and
administering to the patient a treatment effective amount of the compound.

2. The method of claim 1, wherein a and c are a single bond, and b is a double bond.

3. The method of claim 1, further comprising administering the compound is by topical application.

4. The method of claim 1, wherein administration of the compound provides
(i) a blocking effect on AR, and
(ii) an enhanced anabolic activity are obtained.

5. The method of claim 1, wherein administration of the compound provides at least one of the following effects or properties:
(iii) the compound is not aromatized by aromatase;
(iv) the compound is not reduced by 5α-reductase;
(v) the compound inhibits 5α-reductase;
(vi) in the form of its C-17 oxidized metabolite, the compound exhibits enhanced aromatase inhibition.

6. The method of claim 1, wherein the compound is 4-hydroxytestosterone or a salt or ester thereof.

7. The method of claim 6, further obtaining a negative feedback on gonadotropin secretion.

8. The method of claim 1, further comprising administering a second compound selected from the group consisting of an anti-androgen and a 5α-reductase inhibitor.

9. A method for the treatment of a patient having a condition selected from the group consisting of a need for:
enhancing hair growth on the scalp, or reducing hair growth on body regions other than the scalp;

occurrence of disturbed subcutaneous tissue, in particular cellulite;
occurrence of wrinkles or strias of the skin and/or atony of the upper skin;
strengthening, stabilization and/or augmentation of collagen-containing tissues;
for diminution of adipose tissues;
avoidance of body odour; and
achieving skin purity,
the method comprising:
providing a compound selected from compounds having the following formula:

wherein
a, b and c respectively denote, independently from each other, a single bond or a double bond, with the proviso that at least one of a, b and c represents a double bond, and with the proviso that if a is single bond and b is double bond, $R_2$ is not H;
$R_1$ is hydrogen or $C_1$ to $C_6$ alkyl;
$R_2$ is hydrogen or $OR_5$, wherein $R_5$ is hydrogen or $C_1$ to $C_6$ straight chain or branched alkyl;
$R_3$ is, in case of c being a single bond, hydrogen or $C_1$ to $C_6$ alkyl, or in case of c being a double bond, $CHR_5$, wherein $R_5$ is the same as defined before;
$R_4$ is hydrogen, $C_1$ to $C_6$ alkyl, phenyl unsubstituted or substituted by $C_1$ to $C_6$ alkyl, $COR_6$ acyl group ($R_6$ being hydrogen; $C_1$ to $C_6$ straight chain or branched alkyl; phenyl or benzoyl respectively unsubstituted or substituted by $C_1$ to $C_6$ alkyl), or any group leading to hydroxyl upon biological metabolization or chemical deprotection;
and salts and esters thereof; and
administering to the patient a treatment effective amount of the compound.

10. The method of claim 2, wherein the condition is acne.

11. The method of claim 9, wherein a and c are a single bond, and b is a double bond.

12. The method of claim 9, further comprising administering the compound is by topical application.

13. The method of claim 9, wherein administration of the compound provides
(i) a blocking effect on AR, and
(ii) an enhanced anabolic activity are obtained.

14. The method of claim 9, wherein administration of the compound provides at least one of the following effects or properties:
(iii) the compound is not aromatized by aromatase;
(iv) the compound is not reduced by 5α-reductase;
(v) the compound inhibits 5α-reductase;
(vi) in the form of its C-17 oxidized metabolite, the compound exhibits enhanced aromatase inhibition.

15. The method of claim 9, wherein the compound is 4-hydroxytestosterone or a salt or ester thereof.

16. The method of claim 15, further obtaining a negative feedback on gonadotropin secretion.

17. The method of claim 9, further comprising administering a second compound selected from the group consisting of an anti-androgen and a 5α-reductase inhibitor.

18. The method of claim 1, comprising administering to the patient a treatment effective amount of a composition comprising a dimethyl isosorbide and said compound.

19. The method according to claim 18, wherein the compound is 4-hydroxytestosterone or a salt or ester thereof.

20. The method according to claim 18, wherein the composition further comprises a carrier for a topical formulation.

21. The method according to claim 19, wherein the composition further comprises a carrier for a topical formulation.

22. The method according to claim 18, wherein the composition further comprises a second compound selected from the group consisting of an anti-androgen inhibitor and a 5α-reductase inhibitor.

23. The method according to claim 19, wherein the composition further comprises a second compound selected from the group consisting of an anti-androgen inhibitor and a 5α-reductase inhibitor.

24. The method according to claim 20, wherein the composition further comprises a second compound selected from the group consisting of an anti-androgen and a 5α-reductase inhibitor.

25. The method according to claim 21, wherein the composition further comprises a second compound selected from the group consisting of an anti-androgen and a 5α-reductase inhibitor.

26. The method of claim 9, comprising administering to the patient a treatment effective amount of a composition comprising a dimethyl isosorbide and said compound.

27. The method according to claim 26, wherein the compound is 4-hydroxytestosterone or a salt or ester thereof.

28. The method according to claim 26, wherein the composition further comprises a carrier for a topical formulation.

29. The method according to claim 27, wherein the composition further comprises a carrier for a topical formulation.

30. The method according to claim 26, wherein the composition further comprises a second compound selected from the group consisting of an anti-androgen and a 5α-reductase inhibitor.

31. The method according to claim 27, wherein the composition further comprises a second compound selected from the group consisting of an anti-androgen and a 5α-reductase inhibitor.

32. The method according to claim 28, wherein the composition further comprises a second compound selected from the group consisting of an anti-androgen and a 5α-reductase inhibitor.

33. The method according to claim 29, wherein the composition further comprises a second compound selected from the group consisting of an anti-androgen and a 5α-reductase inhibitor.

* * * * *